US008608796B2

(12) United States Patent
Matheny

(10) Patent No.: US 8,608,796 B2
(45) Date of Patent: Dec. 17, 2013

(54) PROSTHETIC TISSUE VALVE

(71) Applicant: Robert Matheny, Norcross, GA (US)

(72) Inventor: Robert Matheny, Norcross, GA (US)

(73) Assignee: CorMatrix Cardiovascular, Inc., Roswell, GA (US)

( * ) Notice: Subject to any disclaimer, the term of this patent is extended or adjusted under 35 U.S.C. 154(b) by 0 days.

(21) Appl. No.: 13/801,242

(22) Filed: Mar. 13, 2013

(65) Prior Publication Data
US 2013/0204358 A1    Aug. 8, 2013

Related U.S. Application Data

(62) Division of application No. 12/875,727, filed on Sep. 3, 2010, now Pat. No. 8,257,434.

(51) Int. Cl.
*A61F 2/24* (2006.01)

(52) U.S. Cl.
USPC ........ 623/2.19; 623/2.12; 623/2.13; 623/2.17

(58) Field of Classification Search
USPC .............. 623/1.24, 2.15, 900, 1.26, 2.1, 623/2.12–2.19
See application file for complete search history.

(56) References Cited

U.S. PATENT DOCUMENTS

| 6,254,636 B1 * | 7/2001 | Peredo .................. 623/2.15 |
| 6,733,525 B2 * | 5/2004 | Yang et al. ............. 623/2.18 |
| 2004/0210306 A1 * | 10/2004 | Quijano et al. ........ 623/2.17 |

* cited by examiner

*Primary Examiner* — David Isabella
*Assistant Examiner* — Yashita Sharma
(74) *Attorney, Agent, or Firm* — Francis Law Group

(57) ABSTRACT

A prosthetic tissue valve for aortic, pulmonary, mitral or tricuspid valve replacement is described herein. A sewing ring for use with the prosthetic tissue valve is also described. The valve can have a circumference that is a predetermined distance larger than the circumference of an annulus in a defective valve. The valve can be substantially planar in an unstressed position before attachment at the annulus and substantially non-planar upon attachment in a biased position at the annulus. Methods are provided for placing the valve as described herein in the biased position within the annulus of the defective valve.

1 Claim, 9 Drawing Sheets

PROSTHETIC TISSUE VALVE

CROSS-REFERENCE TO RELATED APPLICATIONS

This application is a divisional of co-pending U.S. patent application Ser. No. 12/875,727, filed Sep. 3, 2010, which is a continuation-in-part of U.S. patent application Ser. No. 11/958,405, filed Dec. 18, 2007, now abandoned, and U.S. patent application Ser. No. 11/958,407, filed Dec. 18, 2007, now abandoned, and which also claims the benefit of the filing date of U.S. Provisional Patent Application Ser. No. 61/295,503, filed Jan. 15, 2010. Each of the above-referenced patent applications is hereby incorporated herein by reference in its entirety.

FIELD OF THE INVENTION

The invention generally relates to a prosthetic tissue valve for replacing defective aortic, pulmonary, mitral or tricuspid valves. More specifically, the invention relates to a prosthetic tissue valve that is substantially planar prior to implantation in an annulus and substantially non-planar following implantation in an annulus.

BACKGROUND OF THE INVENTION

In general, two types of artificial heart valves are used to replace defective heart valves: mechanical valves and tissue valves. Although implantation of artificial heart valves has traditionally occurred through open heart surgery, research and experimentation are being done to develop valves that can be placed in a patient percutaneously, thereby avoiding open heart surgery.

Implantation of mechanical valves, which are durable, requires open heart surgery, risks peri-valvular leakage on the outside of the valve between the valve and the attachment wall, and requires a lifetime of administration of anti-coagulants, which requires close (usually bi-weekly) monitoring in order to avoid either bleeding or thrombotic/embolic stroke. Mechanical valves also risk development of stenosis at the valve replacement site, and incur chronic hemolysis (damage to red blood cells by the mechanical action of the valve).

Tissue valves typically last from 10 to 15 years in less active and elderly adults and are of porcine or human origin. They fail because the tissue of the valve begins to wear, at least in part because the valves are retrieved after already having undergone partial lifetimes of use. Tissue valves in younger people wear out more quickly due to the more active blood flow in younger people, which causes rapid calcification and places great mechanical demands on the valves. The risk of death or serious complications from surgical valve replacement is typically from 1% to 5% depending on the health of the patient and the skill of the surgeon. Therefore, it is preferred that a valve only be replaced one time.

Mechanical valves last longer in younger patients because the patients are still growing. However, pediatric valve replacements are particularly challenging because the patients frequently outgrow the implanted mechanical valve and require surgical intervention to replace the pediatric valve with a larger valve.

Progressive deterioration of a tissue valve can lead to stenosis, which manifests itself as an obstruction of forward flow through the valve when the valve is in its open position. More commonly, deterioration of a valve produces tears in the valve leaflets that cause regurgitation, which manifests itself as a leakage in the valve when the valve is in its closed position.

Known synthetic valves, although configured to mimic native valves, never assimilate fully into the surrounding tissue following implantation. In addition, attachment of known synthetic valves is accomplished using a ring that remains in a single plane following implantation, thereby risking peri-valvular leakage in the same manner as the attachments of mechanical valves.

The tricuspid valve separates the right atrium from the right ventricle, and the mitral valve separates the left atrium from the left ventricle. The annuluses in which these valves are mounted typically comprise dense fibrous rings that are attached either directly or indirectly to the atrial and ventricular muscle fibers. In a valve replacement operation, the damaged leaflets are excised and the annulus is sculpted to receive a replacement valve. Ideally, the annulus presents relatively healthy tissue which can be formed by a surgeon into a substantially uniform ledge that projects into the opening created after a native valve is removed. The time and spatial constraints imposed by surgery, however, often dictate that the shape of the resulting annulus is less than perfect for attachment of a sewing ring. Moreover, the leaflets of the valve and the annulus may be calcified, and complete annular debridement, or removal of the hardened tissue, can result in a larger opening and a more gradually sloped annulus ledge for attachment of the sewing ring. In short, the contours of the resulting annulus vary widely after the natural valve has been excised.

Conventional placement of a valve is intra-annular, with a valve body deep within the narrowest portion of the annulus to enhance any seal effected by the sewing ring/suture combination and reduce the chance of perivalvular leakage. Surgeons report using at least 30 simple sutures or 20 mattress-type sutures to prevent leakage.

The implantation of a prosthetic heart valve, including mechanical valves and bioprosthetic valves (i.e., "tissue" valve), requires a great deal of skill and concentration given the delicate nature of the native heart tissue, the spatial constraints of the surgical field and the criticality of achieving a secure and reliable implantation. It is of equal importance that the valve have characteristics that promote a long valve life and have minimal impact on the physiological makeup of the heart environment.

Given the uneven nature of the annuluses, the design of the sewing ring and the method by which the sewing ring is fixed into place are perhaps the most crucial aspects of prosthetic heart valve implantation. Due to the inability of conventional sewing rings to easily stretch, if the selected size of the sewing ring is even slightly too small, attachment can only be achieved by placing undue tension on the tissue and sutures. As a result, a great deal of care and accuracy by the surgeon is needed in the selection of a valve size that precisely matches the valve annulus of the patient. Unfortunately, standard sizing tools are provided in increments based on an overall opening size, and may not be able to accurately measure a less than optimally formed annulus. The surgeon thus must select an approximate valve size.

Accordingly, there is a need in the art of valve replacement procedures for a valve having the benefits of a tissue valve and the longevity of a mechanical valve, without the side effects or disadvantages of either. Surgical outcomes would also benefit greatly by an improved sewing ring, permitting improved tissue attachment in all valve replacements.

SUMMARY OF THE INVENTION

In one aspect, a valve disclosed herein is designed to replace a native valve such as the aortic, pulmonary, mitral, or tricuspid valves in the heart of a subject. In one aspect, the valve can have a plurality of leaflets that extend generally inwardly relative to a valve circumference toward a radial center point of the valve such that at least a portion of each leaflet contacts its adjacent leaflets. When placed on a flat surface in an unstressed position before attachment of the valve in the subject, the valve is substantially flat or planar and can therefore, in a further aspect, be formed from a substantially planer material. In one aspect, the valve can have a sewing ring to which the leaflets are attached and the sewing ring can be attached to the valvular annulus at the site of valve replacement. In various aspects, it is contemplated that the sewing ring can be less than about 5 mm wide, and more preferably less than about 1 mm wide, thereby maximizing the portion of the luminal space that is available for blood flow.

In another aspect, the sewing ring and the leaflets of the valve can be made of a biointegrating material such that, over time in the body, the leaflets develop material properties substantially similar to or identical to the material properties of native tissue found in the body of the subject. In one aspect, the biointegrating material used to make the sewing ring and the valve can be an extracellular matrix material.

Although theoretically any extracellular matrix material can be used for this purpose, preferred extracellular matrix materials are exogenous mammalian extracellular matrices, such as those derived from porcine or bovine sources. In one aspect, the extracellular matrices can be derived from such tissues as small intestine submucosa (SIS), stomach submucosa (SS), liver basement membrane (LBM), urinary bladder submucosa (UBS), and in general any other sources of extracellular matrix material that are retrievable from a mammal. The advantage of using the extracellular matrix materials from mammalian sources is that these materials are known to regenerate tissue at the site where they are placed in a human or other mammal. In use, the extracellular matrix material of the sewing ring and the valve can be in communication with the circulation of a subject and can develop into human tissue after about 3 to 6 months in the subject's body. Thus, the regenerated tissue will be like new tissue with the coordinate lifespan of new tissue, and will not need to be replaced. In addition, with pediatric patients, the leaflet tissue can grow with the patient and expand as the patient's heart tissue grows to adult proportions, thus eliminating the risk of needing a second or subsequent surgery to replace the valve or the sewing ring.

In one aspect, the circumference of the valve can be defined by the sewing ring. In this aspect, the circumference of an outer portion of the sewing ring is formed to be larger than the circumference of the annulus of the valve lumen where the replacement is to occur. In one aspect, the circumference of the valve can range from about 60 mm to about 220 mm. The ratio of the operative valve circumference to the annular circumference can range from about 1.01:1 to about 3.00:1. Similarly, the operative valve diameter can be configured to be larger than the diameter of the annulus, and the valve diameter can range from about 20 mm to about 70 mm. Optionally, the ratio of the operative valve diameter to the diameter of the annulus of the valve lumen can range from about 1.01:1 to about 3.00:1.

In another aspect, although the claimed valve and sewing ring are generally planar in an unstressed position outside the body, upon attachment of the valve to the annulus in a biased position, they become substantially non-planar. In this aspect, when the valve is attached to the annulus in the biased position, the valve is configured to function much like a native valve and work to control blood flow like a native valve does. Thus, using either intermittent or continuous attachment points (such as suture), the edge of the valve is attached to the interior wall of the annulus in a sinusoidal or wave-like pattern so that each leaflet has substantially consistent high and low attachment points that vary from the plane of the annulus. This attachment means forms leaflets that are configured to form a valve in the annulus that will approximate or mimic the characteristics of a native tissue valve having native tissue leaflets with a rise and fall of leaflet tissue providing for a substantially unidirectional flow of blood into a right ventricle, pulmonary artery, left ventricle, and aorta.

Preferred attachment means include using multiple sutures along the sewing ring, forming attachment of the sewing ring in an up and down configuration along the annular region to generally position the sewing ring at the location of the annulus of the defective valve, and directing three-dimensional structural formation of the leaflets, which structure directs the leaflets to function similarly to the function of native leaflets in healthy native valves.

In operation, an edge portion of the valve can be wrapped around or otherwise attached to the sewing ring, if a sewing ring is used. In one aspect, where the sewing ring is constructed of extracellular matrix material, the extracellular matrix material can be rolled to form several layers in a tubular configuration forming the sewing ring by attachment of the two ends of the rolled material. Alternatively, additional ring-like pieces can be formed from extracellular matrix material and can be laminated or otherwise coupled to the edge portion of the valve to form the sewing ring. As a still further alternative, a circular or linear strip of material having a width can be sewn, glued, or otherwise attached to itself, thereby forming a tear drop-like tube that extends for a length and can either be attached at the two ends of the extracellular matrix material or extend for a circular distance in a ring formation.

BRIEF DESCRIPTION OF THE DRAWINGS

These and other features of the preferred embodiments of the invention will become more apparent in the detailed description in which reference is made to the appended drawings wherein.

DETAILED DESCRIPTION OF THE INVENTION

Figure 1:
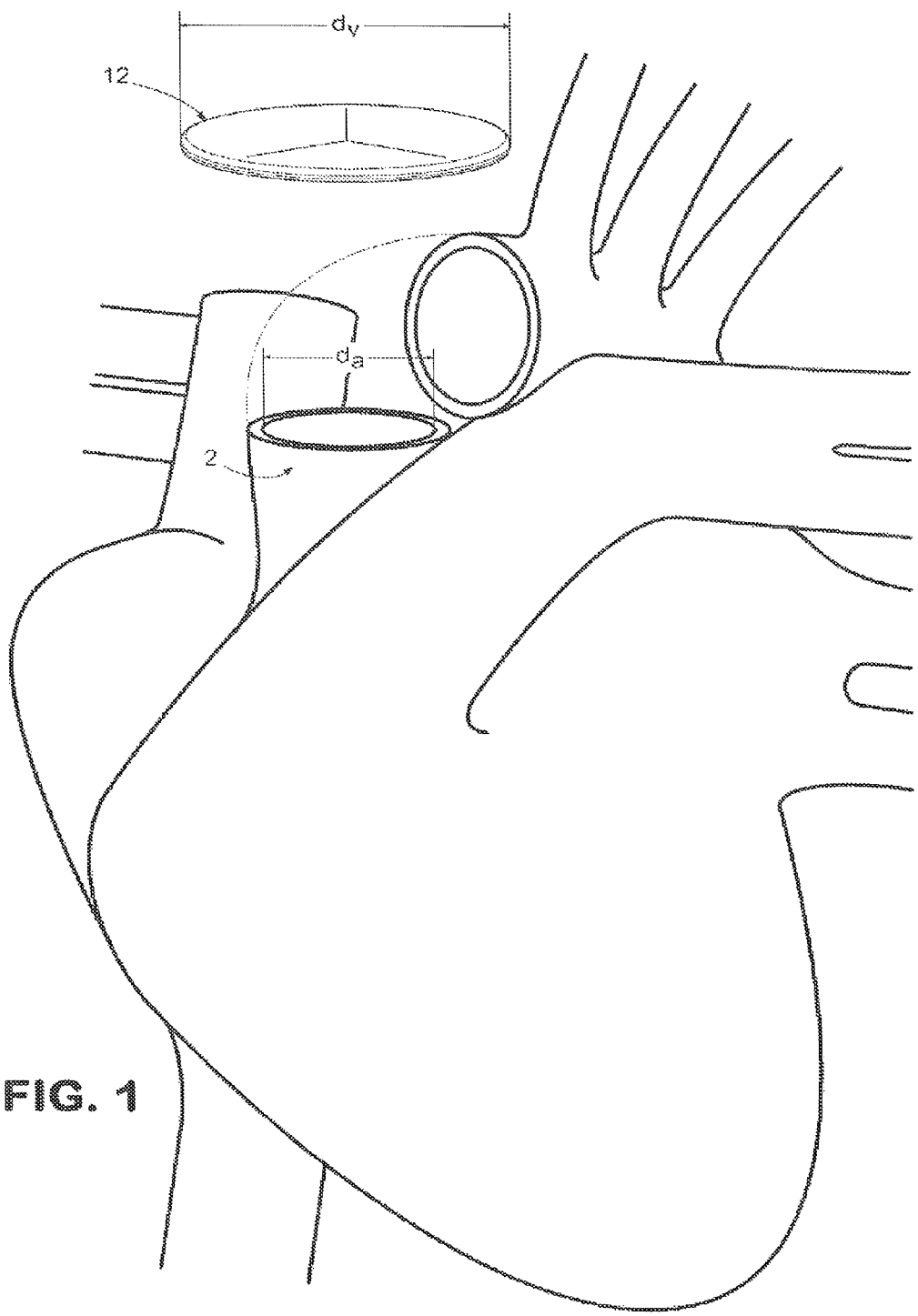
FIG. 1 depicts a perspective view of a valve as described herein positioned relative to an annulus of the heart.

The present invention may be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

As used in the specification and the appended claims, the singular forms "a," "an" and "the" include plural referents unless the context clearly dictates otherwise. Thus, for example, reference to a "leaflet" can include two or more such leaflets unless the context indicates otherwise.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims. Except as specifically defined herein, all technical and scientific terms used herein are to be given as broad a commonly understood meaning as possible while maintaining claim validity.

Described herein are valves and replacement leaflets for controlling fluid flow in a lumen having an annulus. In one aspect, the valve is suitable for replacing an aortic, pulmonary, mitral, or tri-cuspid valve in the heart of a subject. In another aspect, the valve can comprise at least one leaflet configured to selectively prevent undesired regurgitation of blood flow therethrough the valve. For example, the valve can comprise a single leaflet that is sized to prevent blood flow therethrough the valve when the leaflet is selectively positioned in a blocking position. Alternatively, the valve can comprise a plurality of leaflets. Optionally, the at least one leaflet can be attached to a sewing ring. In a further aspect, a single leaflet as described herein can be used as a replacement leaflet for controlling fluid flow through an annulus. In a further aspect, the valve can have a circumference and a diameter that are larger than the circumference and diameter of the annulus.

Figure 6:
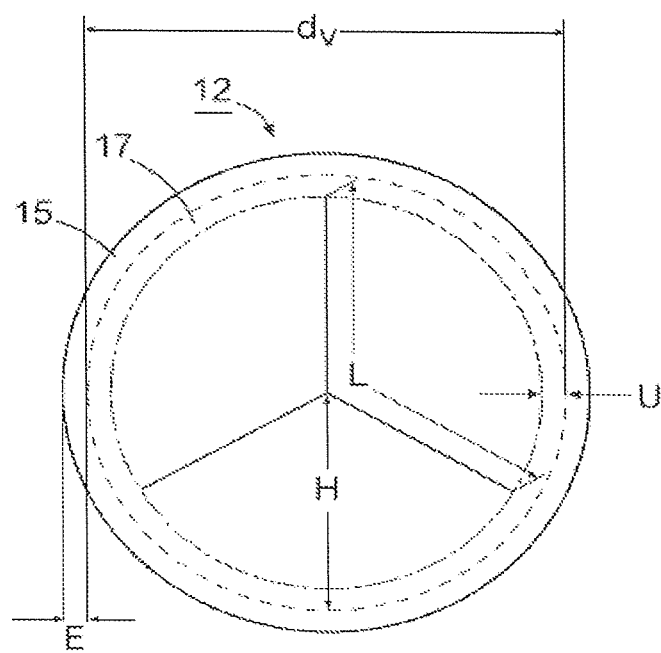
FIG. 6 depicts a top view of an exemplary planar valve with substantially triangular leaflets prior to folding of the outer edge portion of the valve, as described herein.
Figure 7:
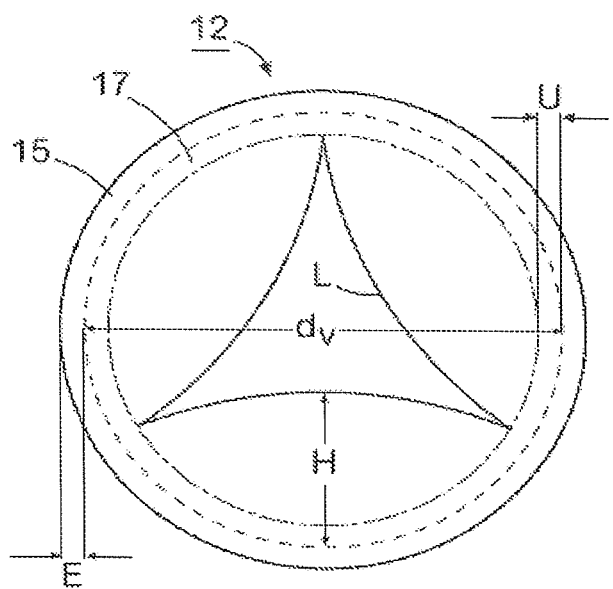
FIG. 7 depicts a top view of an exemplary planar valve with substantially rounded leaflets prior to folding of the outer edge portion of the valve, as described herein.

In one aspect, as shown in FIGS. 6 and 7, it is contemplated that the leaflets of the valve 12 can be created from a substantially planar piece of material, such as, for example and without limitation, a substantially planar piece of extracellular matrix material as defined herein. In this aspect, the leaflets can be defined by cutting or stamping out selected portions of the planar piece of material using conventional techniques. For example, as depicted in FIG. 6, the leaflets of the valve 12 can be cut from the substantially planar piece of material in substantially triangular shapes. Alternatively, as depicted in FIG. 7, the leaflets of the valve 12 can have substantially rounded shapes.

In another aspect, and with reference to FIGS. 6 and 7, prior to preparation of the valve 12 for implantation within the annulus 2, a circumference and, thus, an outer edge portion 15 of the valve can be defined. In this aspect, the outer edge portion 15 of the valve 12 can have a width E that ranges from about 3 mm to about 6 mm, and more preferably is about 5 mm. It is contemplated that the outer edge portion 15 of the valve can be rolled to create an attachment surface. In one aspect, the attachment surface can be configured for direct attachment thereto the annulus 2. Alternatively, the attachment surface can be configured for attachment thereto a sewing ring.

Optionally, in one exemplary aspect, as depicted in FIGS. 6 and 7, during the process of defining the leaflets and outer edge portion, an uncut portion 17 along the operative circumference of the valve 12 can also be defined. In this aspect, the uncut portion 17 can have a substantially consistent width U along the operative circumference of the valve 12. Where an uncut portion 17 is defined in the valve 12, it is contemplated that the width U of the uncut portion can range from about 1 mm to about 6 mm, and more preferably from about 4 mm to about 5 mm.

Figure 2A:
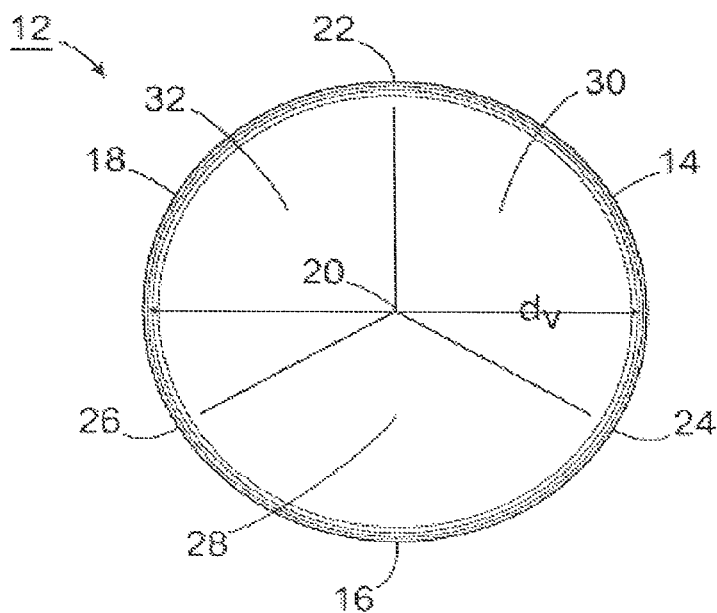
FIG. 2A depicts a top view of an exemplary planar valve with substantially triangular leaflets in an unstressed position before implantation in an annulus in a non-planar configuration, as described herein.
Figure 4A:
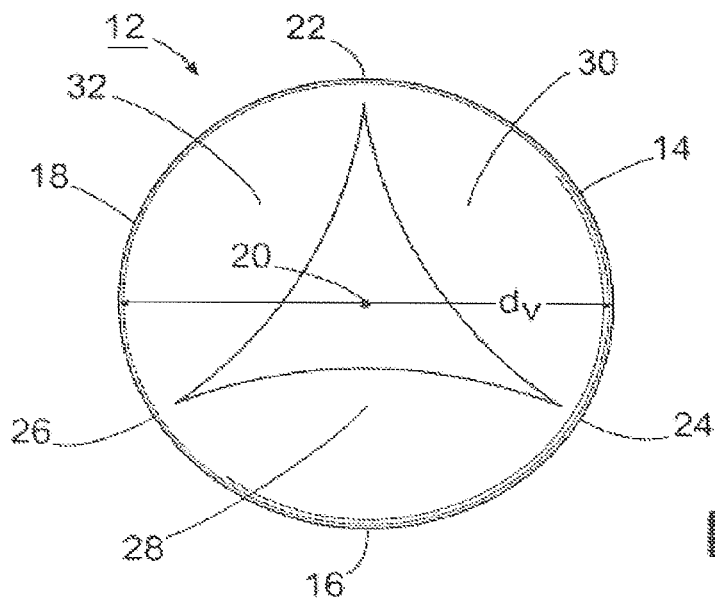
FIG. 4A depicts a top view of an exemplary planar valve with substantially rounded leaflets in an unstressed position before implantation in an annulus in a non-planar configuration, as described herein.

FIGS. 2A and 4A each depict an exemplary valve 12 as it appears after it has been prepared for implantation (after the outer edge of the valve has been rolled up) but before attachment to the annulus 2. More particularly, FIG. 2A depicts an exemplary valve 12 having substantially triangular leaflets, while FIG. 4A depicts an exemplary valve having substantially rounded leaflets. It is contemplated that the circumference of the valve 12 following the rolling of the outer edge portion 15 of the valve can correspond to an operative circumference of the valve. Similarly, the diameter of the valve 12 following the rolling of the outer edge portion 15 of the valve can correspond to an operative diameter ($d_v$) of the valve. As used herein, the operative diameter ($d_v$) of the valve 12 corresponds to the portion of the valve that is configured to span across the annulus 2 after attachment of the valve thereto the annulus. Thus, as used herein, the operative diameter ($d_v$) does not factor in outer edge portion 15, which is rolled up prior to attachment of the valve 12 thereto the annulus 2.

In another aspect, the valve 12 can comprise at least one leaflet. In this aspect, the at least one leaflet can comprise a plurality of leaflets. In an additional aspect, leaflets 28, 30, and 32 can have distal end portions that extend inwardly relative to the circumference of the valve generally toward a radial center 20 of the valve.

Optionally, the valve 12 can comprise a sewing ring 40. In one aspect, the sewing ring 40 can be attached to the rolled up outer edge portion 15 of the valve 12. In another aspect, before attachment to the annulus, the sewing ring 40 can be substantially semi-lunar or circular with an inner portion and an outer portion. In this aspect, the inner portion of the sewing ring can be attached to the valve, while the outer portion of the sewing ring 40 can define an operative circumference of the sewing ring and, thus, the operative circumference of the valve 12. Similarly, the outer diameter of the sewing ring 40 can define the operative diameter of the sewing ring and, thus, the operative diameter ($d_v$) of the valve 12.

Figure 2B:
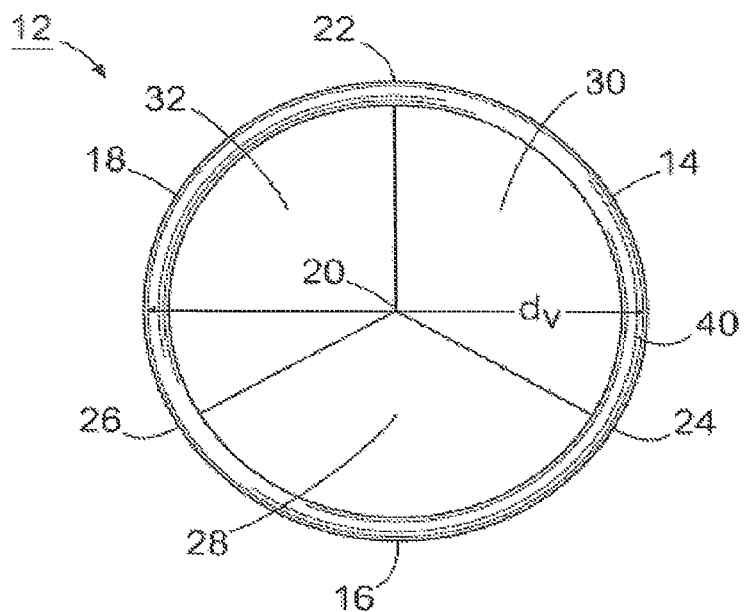
FIG. 2B depicts a top view of an exemplary planar valve with substantially triangular leaflets and a sewing ring in an unstressed position before implantation in an annulus in a non-planar configuration, as described herein.
Figure 4B:
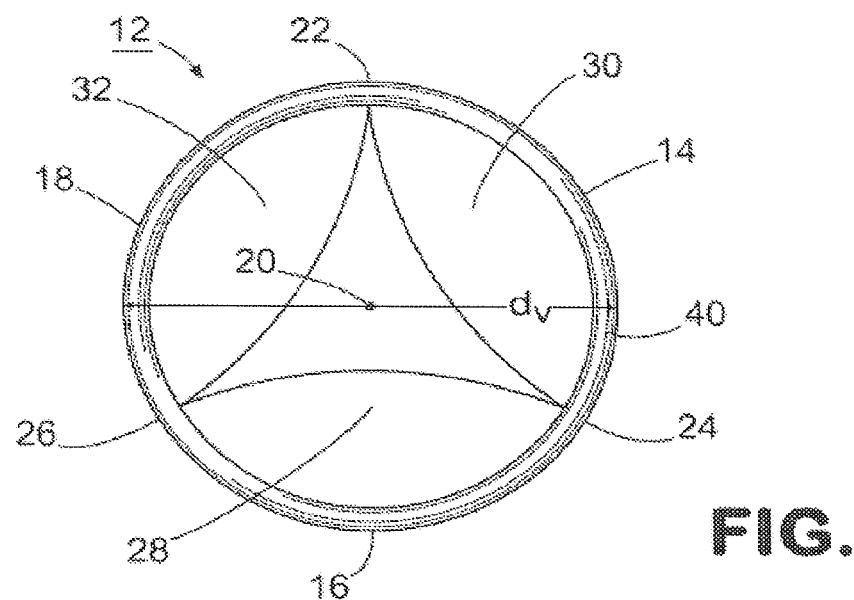
FIG. 4B depicts a top view of an exemplary planar valve with substantially rounded leaflets and a sewing ring in an unstressed position before implantation in an annulus in a non-planar configuration, as described herein.

FIGS. 2B and 4B depict valve 12 and sewing ring 40 as they are before attachment to the annulus. More particularly, FIG. 2B depicts an exemplary valve 12 having substantially triangular leaflets and sewing ring 40, while FIG. 4B depicts an exemplary valve having substantially rounded leaflets and sewing ring 40. In one aspect, the valve 12 can comprise at least one leaflet. In this aspect, the at least one leaflet can comprise a plurality of leaflets. In one aspect, leaflets 28, 30, and 32 can have distal end portions that extend inwardly relative to the inner portion of the sewing ring 40 generally toward a radial center 20 of the valve.

In one aspect, the operative circumference of the valve 12 can be larger than the circumference of the annulus. In this aspect, when the annulus is located in a heart valve, including, for example and without limitation, an aortic valve, a pulmonary valve, a tricuspid, or a bicuspid (mitral) valve, the ratio of the operative circumference of the valve to the circumference of the annulus can range from about 1.01:1 to about 3.00:1, more preferably from about 1.40:1 to about 2.40:1, and most preferably from about 1.70:1 to about 2.10:1. In addition to the ratios serving as the endpoints of the ranges set forth above, the disclosed ranges also include all ratios falling between the endpoint ratios. It is contemplated that, because the operative circumference of the valve 12 is greater than the circumference of the annulus 2, the valve can form a substantially sinusoidal or wave-like pattern upon attachment to the annulus in the biased position. In another aspect, the operative circumference of the valve can range from about 60 mm to about 220 mm, more preferably from about 80 mm to about 190 mm, and most preferably from about 100 mm to about 140 mm. Optionally, it is contemplated that the valves and sewing rings described herein can be provided in a series of different circumferences, thereby permitting a surgeon to select an appropriately sized valve or sewing ring depending on the dimensions of the annulus, which can be determined during a surgical procedure.

Figure 3A:
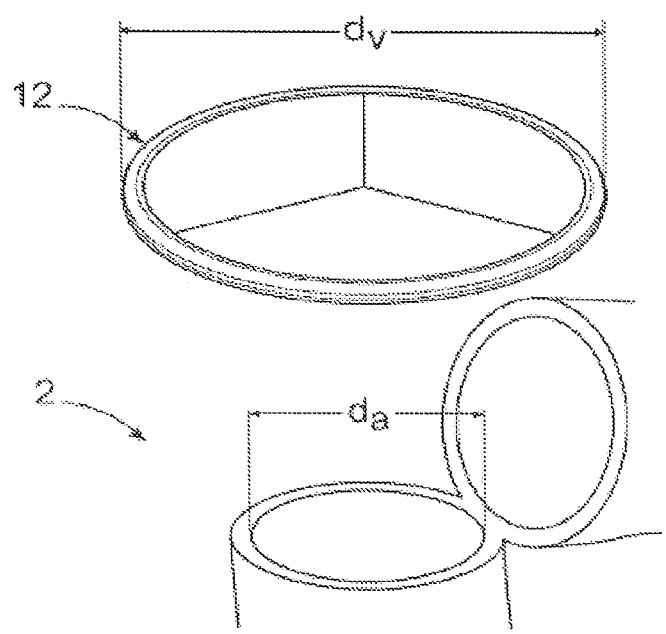
FIG. 3A depicts a perspective view of the valve of FIG. 2B positioned relative to an annulus of the heart.
Figure 5A:
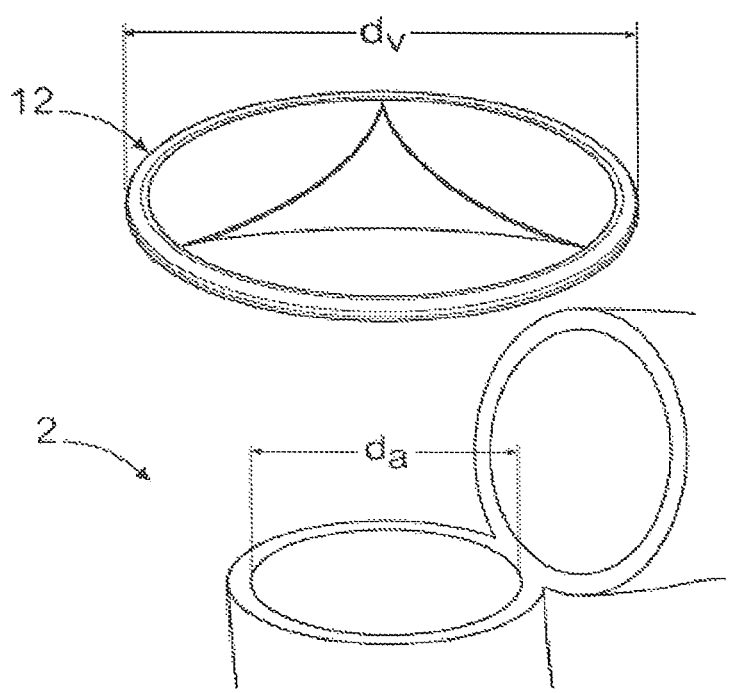
FIG. 5A depicts a perspective view of the valve of FIG. 4B positioned relative to an annulus of the heart.

Similarly, in another aspect, and as shown in FIGS. 3A and 5A, the operative diameter ($d_v$) of the valve 12 can be greater than the diameter ($d_a$) of the annulus 2. In this aspect, when the annulus is located in a heart valve, including, for example and without limitation, an aortic valve, a pulmonary valve, a tricuspid, or a bicuspid (mitral) valve, the ratio of the operative diameter ($d_v$) of the valve to the diameter ($d_a$) of the annulus 2 can range from about 1.01:1 to about 3.00:1, more preferably from about 1.40:1 to about 2.40:1, and most preferably from about 1.70:1 to about 2.10:1. In addition to the ratios serving as the endpoints of the ranges set forth above, the disclosed ranges also include all ratios falling between the endpoint ratios. In another aspect, the operative diameter ($d_v$) of the valve can range from about 20 mm to about 70 mm, more preferably from about 25 mm to about 60 mm, and most preferably from about 35 mm to about 45 mm. Optionally, it is contemplated that the valves and sewing rings described herein can be provided in a series of different diameters, thereby permitting a surgeon to select an appropriately sized valve or sewing ring depending on the dimensions of the annulus, which can be determined during a surgical procedure.

As shown in FIGS. 6-7, in one aspect, each leaflet can have an edge length L corresponding to the total length of an inner edge of each leaflet that extends inwardly relative to the operative circumference of the valve 12 generally toward a radial center 20 of the valve. In an additional aspect, when the leaflets are substantially triangular as shown in FIG. 6, the edge length L of each leaflet can range from about 10 mm to about 70 mm, more preferably from about 15 mm to about 60 mm, and most preferably from about 25 mm to about 45 mm. In this aspect, it is contemplated that the ratio between the edge length L of each leaflet to the diameter ($d_a$) of the annulus 2 can range from about 0.5:1 to about 3:1, and more preferably from about 1:1 to about 2:1. In addition to the ratios serving as the endpoints of the ranges set forth above, the disclosed ranges also include all ratios falling between the endpoint ratios. In another aspect, when the leaflets are substantially rounded as shown in FIG. 7, the edge length L of each leaflet can range from about 15 mm to about 60 mm, more preferably from about 20 mm to about 50 mm, and most preferably from about 25 mm to about 35 mm. In this aspect, it is contemplated that the ratio between the edge length L of each leaflet to the diameter ($d_a$) of the annulus 2 can range from about 1:1 to about 2:1, and more preferably from about 1.20:1 to about 1.40:1. In addition to the ratios serving as the endpoints of the ranges set forth above, the disclosed ranges also include all ratios falling between the endpoint ratios.

In an additional aspect, and as shown in FIGS. 6-7, each leaflet can have a height H. In this aspect, it is contemplated that each leaflet can have an apex corresponding to the point along edge length L of each leaflet that is farthest from the operative circumference of the valve 12, and the height H of each leaflet can correspond to the distance between the apex of each leaflet and the operative circumference of the valve. In one aspect, when the leaflets are substantially triangular as shown in FIG. 6, the height H of each leaflet can range from about 10 mm to about 35 mm, more preferably from about 12 mm to about 30 mm, and most preferably from about 17 mm to about 23 mm. In this aspect, it is contemplated that the ratio between the height H of each leaflet to the diameter ($d_a$) of the annulus 2 can range from about 0.3:1 to about 2:1, more preferably from about 0.5:1 to about 1.5:1, and most preferably from about 0.7:1 to about 1.1:1. In addition to the ratios serving as the endpoints of the ranges set forth above, the disclosed ranges also include all ratios falling between the endpoint ratios. Optionally, in this aspect, it is contemplated that the ratio between the height H of each leaflet and the width U of the uncut portion 17 can range from about 2:1 to about 7:1, and more preferably from about 4:1 to about 5:1. In addition to the ratios serving as the endpoints of the ranges set forth above, the disclosed ranges also include all ratios falling between the endpoint ratios. In another aspect, when the leaflets are substantially rounded as shown in FIG. 7, the height H of each leaflet 28, 30, 32 can range from about 5 mm to about 30 mm, more preferably from about 10 mm to about 25 mm, and most preferably from about 12 mm to about 18 mm. In this aspect, it is contemplated that the ratio between the height H of each leaflet to the diameter ($d_a$) of the annulus 2 can range from about 0.3:1 to about 1:1, more preferably from about 0.4:1 to about 0.9:1, and most preferably from about 0.5:1 to about 0.8:1. In addition to the ratios serving as the endpoints of the ranges set forth above, the disclosed ranges also include all ratios falling between the endpoint ratios. Optionally, in this aspect, it is contemplated that the ratio between the height H of each leaflet and the width U of the uncut portion 17 can range from about 1:1 to about 5:1, and more preferably from about 3:1 to about 4:1. In addition to the ratios serving as the endpoints of the ranges set forth above, the disclosed ranges also include all ratios falling between the endpoint ratios.

Figure 3B:
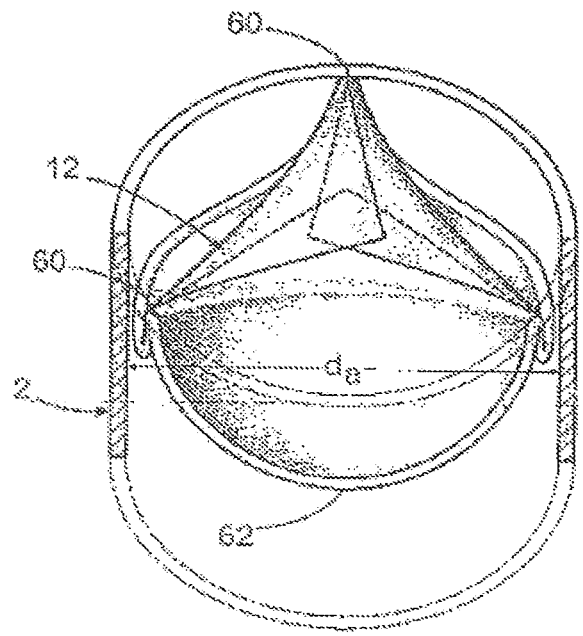
FIG. 3B depicts a perspective view of the valve of FIG. 2B in a biased, non-planar position following implantation in the annulus of the heart, as described herein.
Figure 3C:
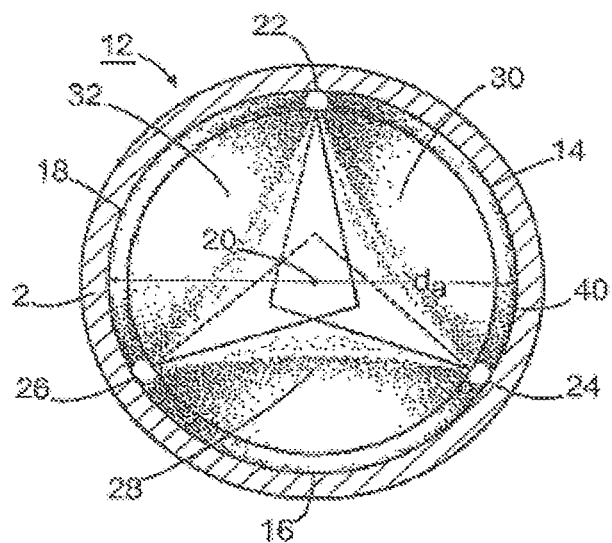
FIG. 3C depicts a top view of the valve of FIG. 3B.
Figure 5B:
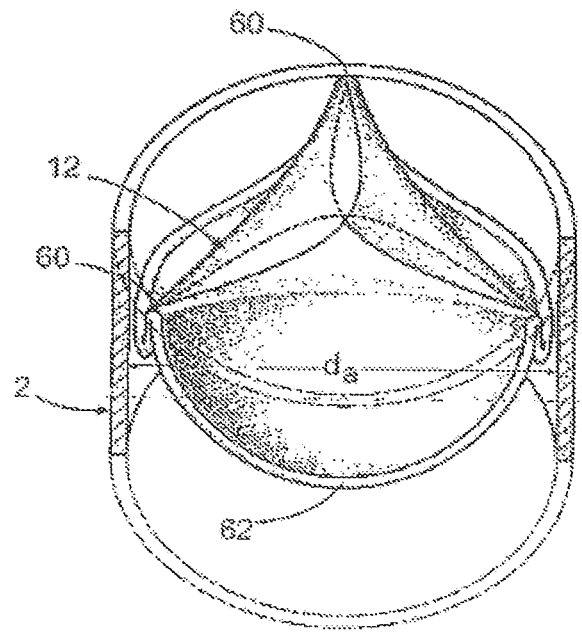
FIG. 5B depicts a perspective view of the valve of FIG. 4B in a biased, non-planar position following implantation in the annulus of the heart, as described herein.
Figure 5C:
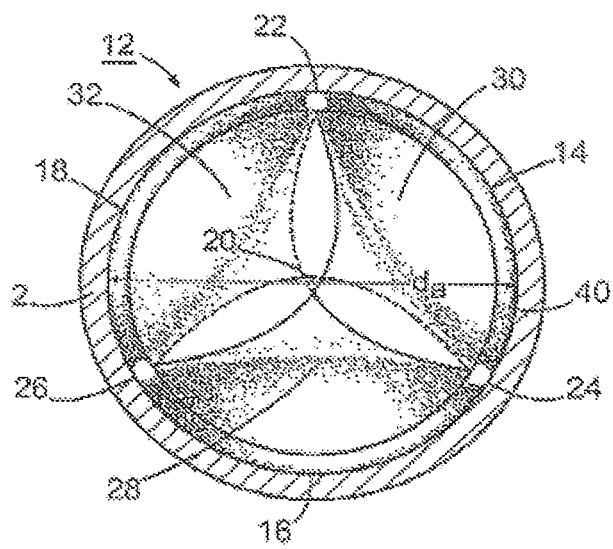
FIG. 5C depicts a top view of the valve of FIG. 5B.

In a further aspect, attachment of the valve 12 can occur at a plurality of attachment points on the operative circumference of the valve, such as points 22, 24, and 26, as depicted in FIGS. 2A, 2B, and 3C for a valve having substantially triangular leaflets as described herein, and in FIGS. 4A, 4B, and 5C for a valve having substantially curved leaflets as described herein. Points 22, 24, and 26 can be radially aligned with points where adjacent leaflets 28, 30, and 32 contacted one another prior to attachment of the valve 12 thereto the interior surface of the annulus 2. In this aspect, for a valve 12 having a sewing ring 40, attachment of the valve can occur at a plurality of attachment points on the outer portion of the sewing ring. As depicted in FIGS. 3B and 5B, the outer edge portion of the valve 12 can be attached to the interior wall of the valve annulus 2 in a substantially sinusoidal or wave-like pattern. It is contemplated that the substantially sinusoidal pattern formed by the valve 12 can promote substantially unidirectional blood flow therethrough the valve. It is further contemplated that blood flow can occur through the annulus 2 in an axial direction from points 14, 16, and 18 to points 22, 24, and 26.

In one aspect, it is contemplated that the plurality of attachment points can be substantially equally spaced along the circumference of the valve. In this aspect, for a valve 12 having a sewing ring 40, the plurality of attachment points can be substantially equally spaced along the outer portion of the sewing ring. In another aspect, the plurality of attachment points can comprise at least three attachment points. In a further aspect, the plurality of attachment points can comprise six attachment points corresponding to points 22, 24, 26 and also points 14, 16 and 18. It is contemplated that more points in between these equally spaced points can also be used for attachment consistent with the wave-like pattern formed by the sewing ring when the valve is attached in the biased position. In another aspect, the spacing between the attachment points of the plurality of attachment points can be minimized such that the attachment points are placed substantially contiguously along the outer portion of the sewing ring. Attachment can be, without limitation, by suture using absorbable or permanent sutures. The exact knot tying technique can be selected at the preference of the operating physician.

As shown in FIGS. 3B and 5B, it is contemplated in one aspect, that the valve 12, in the biased position, will be attached to the interior surface of the annulus such that the first portions 60 of the outer edge portion of the valve that are adjacent to the base juncture of the respective adjoining leaflets of the valve are positioned substantially co-planar relative to each other or are generally the most upstream portion of the outer edge portion of the valve. In this aspect, the medial portions 62 of the outer edge portion of the valve 12 (medial between the respective adjoining first portions) would extend downward and be coupled to the interior surface of the annulus 2 at a position downstream of the first portions of the outer edge portion of the valve. In one aspect, the medial portions of the outer edge portion of the valve can be substantially co-planar to each other downstream of the first portions of the outer edge portion of the valve.

In a further aspect, and with reference to FIGS. 3B-3C and 5B-5C, upon attachment of the valve thereto the annulus in the biased position, at least a portion of leaflets 28, 30, and 32 can be superposed relative to at least a portion of adjacent leaflets. In this aspect, it is contemplated that, in the biased position, at least a portion of leaflets 28, 30, and 32 can be superposed relative to at least a portion of the other leaflets of the at least one leaflet, including non-adjacent leaflets. It is further contemplated that, in the biased position, at least a portion of leaflets 28, 30, and 32 can underlie at least a portion of the adjacent leaflets of the at least one leaflet. It is still further contemplated that, in the biased position, at least a portion of leaflets 28, 30, and 32 can overlie at least a portion of the adjacent leaflets of the at least one leaflet. In another aspect, it is contemplated that the leaflets are configured such that, upon attachment of the valve thereto the annulus in the biased position, the leaflets can selectively move to an overlapping or otherwise blocking position that is sufficient to selectively prevent undesired regurgitation blood flow therethough the valve. In a further aspect, it is contemplated that the sinusoidal method of attaching the valve in the biased position can produce a tight and conforming fit between the valve and the annulus such that the likelihood of perivalvular leakage is reduced.

With reference to FIGS. 2A-3A and 4A-5A, it is contemplated that, in one aspect, the valve 12 can be substantially planar in an unstressed or pre-insertion position before attachment to an interior surface of an annulus 2 of a valvular lumen. As illustrated in FIGS. 3B-3C and 5B-5C, it is contemplated that the valve can be substantially non-planar upon attachment in a biased position at the annulus. In another aspect, the distal end portions of the respective leaflets can be configured to ensure adequate operational overlay with the other leaflets to prevent undesired directional passage of blood therethough the valve when the valve is attached to the annulus in the biased position. It is also contemplated that portions of the distal edges of the respective leaflets can partially overlap other respective leaflets or can otherwise be in contact with each other to effect the desired directional passage of blood therethough the valve. Although not specifically indicated in FIGS. 3C and 5C, it is contemplated that the portion of each leaflet that overlies or underlies adjacent leaflets can be curved in a manner consistent with the curvature of the remainder of the leaflet.

In one aspect, the valve 12, including the sewing ring 40 and the leaflets 28, 30, and 32, can comprise a biointegrating material. In another aspect, the biointegrating material can comprise an extracellular matrix material. In a further aspect, the extracellular matrix material can comprise mammalian extracellular matrix material that is obtained from mammalian tissue sources. In one exemplary embodiment, the sewing ring and the leaflets comprise mammalian extracellular matrix material.

Mammalian tissue sources are in general any tissue having an extracellular matrix that can be isolated from the mammal and decellularized. Thus, for example, mammalian organs are tissue sources. For example and without limitation, the tissue sources can be any mammalian tissue, for example and without limitation, the small intestine, large intestine, stomach, lung, liver, kidney, pancreas, placenta, heart, bladder, prostate, tissue surrounding growing enamel, tissue surrounding growing bone, fetal tissue from any mammalian organs, and the like.

The forms of the extracellular matrices that make up the extracellular matrix material are, without limitation, generally particulates, liquids, gels, pastes, emulsions, or suspensions. Liquid extracellular matrices are generally thin emulsions or suspensions that are injectable and fluid. Suspension, emulsion or gel extracellular matrices can be substantially thicker and have more body and substance than liquids, but suspensions, emulsions or gels can also be injected if they are not too thick. Extracellular matrices in the form of pastes or near-solid gels or plugs are more concentrated than liquids or injectable emulsions. Particulate extracellular matrices are powders that are formed from a lyophilized sheet of extracellular matrix material that is broken up into fine powder or particulate. Particulates can be used dry as a powder. Particulate extracellular matrices can also be reconstituted in a suitable buffer such as saline to transition into a liquid or semi-solid form.

Extracellular matrix material can be obtained from the tissues of mammals by processes such as described in U.S. Pat. No. 5,554,389, U.S. Pat. No. 4,902,508, and U.S. Pat. No. 5,281,422, which are specifically incorporated by reference in their entirety. Enamel matrices are described in U.S. Pat. No. 7,033,611 and U.S. Patent Publication No. 2005/0043216, which are specifically incorporated by reference in their entirety. For example, the urinary bladder submucosa (UBS) is an extracellular matrix that has the tunica mucosa (which includes the transitional epithelial layer and the tunica propria), a submucosal layer, three layers of muscularis, and the adventitia (a loose connective tissue layer). This general configuration is true also for small intestine submucosa (SIS) and stomach submucosa (SS). However, it is contemplated that any configuration of extracellular matrix tissue layers, including, for example and without limitation, epithelial basement membrane, tunica propria, stratum compactum, lamina muscularis mucosa, tunica submucosa, tunica muscularis, and tunica serosa, can be used to produce the extracellular matrix material.

Other sources of extracellular matrix material include tissues such as the liver and pancreas, which have an additional tissue layer called a basement membrane. For example, the extracellular matrix material can comprise the liver basement membrane (LBM) of mammals prepared by the process described in U.S. Pat. No. 6,379,710, which is specifically incorporated by reference in its entirety. Basement membranes generally do not demonstrate the kind of tensile strength found in submucosa. However, other useful properties may be opportunistically employed from the extracellular matrices of such tissues as the liver, pancreas, placenta and lung tissues, all of which have either basement membrane for extracellular matrix or interstitial membrane (as with the lung). For example, pancreatic extracellular membranes support beta islet cells which are critical to pancreatic function. Also, for example, the liver is one tissue known to be able to regenerate itself and, therefore, special qualities may be present in the LBM that help facilitate that process. The extracellular matrices surrounding developing tooth enamel and developing bone also have particular advantages over other matrices in that they support the growth and differentiation of the hard tissues of bone and enamel.

In some aspects, the extracellular matrix material can be from dermis. For example, AlloDerm®, produced by LifeCell Corporation, is an acellular tissue matrix which is produced from normal human skin using processing techniques established to remove the epidermis and cells within the dermis without significantly altering the normal biochemistry and molecular architecture of the connective tissue matrix. The resulting product is in a freeze-dried form allowing extended shelf life and ease of shipping without degradation or loss of the normal tissue matrix components. AlloDerm® can retain decorin, hyaluronic acid, chondroitin sulfates, nidogen, growth factors and other biochemical proteins present in normal soft tissues. Additionally, AlloDerm® can contain the basement membranes of vascular channels and the orientation of elastin and collagen fibers of the starting dermal tissue.

In some aspects, the extracellular matrix material can be obtained from fascia. In some aspects, the extracellular matrix material can be from parenchymal tissue. In other aspects, the extracellular matrix material can be from pericardium. In still other aspects, the extracellular matrix material can be myocardial extracellular matrix. In additional aspects, the extracellular matrix material can be from decellularized heart tissue, produced, for example, by coronary artery perfusion with detergents (Ott, H C, et al. Nat Med. 2008 February; 14(2):213-21).

In some aspects, the extracellular matrix material can comprise a collagen scaffold derived from a mammalian tissue or organ source. The collagen scaffold can in some aspects comprise the basement membrane of the mammalian tissue source.

In some aspects, the extracellular matrix material can be produced in vitro. For example, the extracellular matrix material can be produced from a culture of mammalian cells. The extracellular matrix material can be produced from proteins extracted from mammalian tissue/organs. For example, in some aspects, the extracellular matrix material comprises an artificial collagen scaffold synthesized from collagen extracted from a mammalian tissue or organ source. Collagen from mammalian sources can be retrieved from matrix-containing tissues and used to form a matrix composition. Extracellular matrices can be synthesized from cell cultures as in the product manufactured by Matrigel™. In addition, dermal extracellular matrix material, subcutaneous extracellular matrix material, large intestine extracellular matrix material, placental extracellular matrix material, omentum extracellular matrix material, heart extracellular matrix material, and lung extracellular matrix material, can be used, derived and preserved similarly as described herein for the SIS, SS, LBM, and UBS materials. Other organ tissue sources of basement membrane for use in producing the extracellular matrix material include the spleen, lymph nodes, salivary glands, prostate, pancreas and other secreting glands. In general, any tissue of a mammal that has an extracellular matrix can be used for developing the extracellular matrix material.

Collagenous matrix can be selected from a variety of commercially available collagen matrices or can be prepared from a wide variety of natural sources of collagen. Collagenous matrix for use in accordance with the disclosed compositions and methods can comprise highly conserved collagens, glycoproteins, proteoglycans, and glycosaminoglycans in their natural configuration and natural concentration. Collagens can be from animal sources, from plant sources, or from synthetic sources, all of which are available and standard in the art.

The extracellular matrix material can be made from a plurality of mammalian tissue sources. Specifically, the extracellular matrix material can be made from two mammalian tissue sources, three mammalian tissue sources, four mammalian tissue sources, five mammalian tissue sources, six mammalian tissue sources, and conceivably up to ten or more tissue sources. These tissue sources can be from the same mammal (for example the same cow, the same pig, the same rodent, the same human, etc.), different mammalian animals of the same species, (e.g. cow 1 and cow 2, pig 1 and pig 2, rodent 1 and rodent 2, human 1 and human 2, etc.), or different species of mammals (for example LBM from a pig, SIS from a cow, and UBS from a dog), all mixed together to form the extracellular matrix material).

The extracellular matrix material can also be a gel matrix combined with a particulate matrix, where the gel is applied to a space or cavity and dusted with powder-like particulates to increase the concentration of matrix at the surface of the cavity. The extracellular matrix material can be two or more liquid matrices (from different tissue sources) combined together. The extracellular matrix material can be two or more suspension matrices (from different tissue sources) combined together. The extracellular matrix material can be two or more particulate matrices (from different tissue sources) combined together. The particulate matrices combined together can be applied to an annulus as a particulate or as a rehydrated suspension, where saline or other suitable buffer is applied to the particulate mixture and that hydrated composition is applied to the annulus in the individual being treated. The particulate can also be dusted onto a sheet of matrix before or after placement at the annulus. The extracellular matrix material can be a liquid mixture of two or more extracellular matrices. With this dusting embodiment, the liquid, gel, suspension or emulsion can be from a single mammalian tissue source, and dusted with a particulate extracellular matrix from either the same or a different mammalian tissue source. Accordingly, the suspension, emulsion, gel or liquid can be SIS, and the particulate can be SIS, or the suspension, emulsion, gel or liquid can be SIS and the particulate can be SS, or LBM, or UBS. The suspension, emulsion, gel or liquid can be a mixture of SIS and LBM and the particulate for dusting can be from SS. These examples are not meant to be exhaustive of the possible combinations of elements in the extracellular matrix material.

The extracellular matrix material can further include one or more additional components to aid in some aspect of the tissue regenerative process or the generation of new tissue, however the biological activity is characterized. The additional component can be any component that somehow serves the extracellular matrix material and its purpose in the mammalian body. Thus, the additional component can help to regenerate tissue, heal a wound, better recruit stem cells, manipulate the immune environment in a beneficial way, therapeutically treat the local environment, or otherwise contribute to some aspect of the process for which the extracellular matrix material is being used.

In one aspect, the additional component can be one or more cells. In some aspects, the additional component can be non-native cells, i.e., cells that are heterologous to the mammalian ECM. In some aspects, the additional component can be stem cells. A non-exhaustive list of stem cells include a human embryonic stem cell, a fetal cardiomyocyte, a myofibroblast, a mesenchymal stem cell, an autotransplanted expanded cardiomyocyte, an adipocyte, a totipotent cell, a pluripotent cell, a blood stem cell, a myoblast, an adult stem cell, a bone marrow cell, a mesenchymal cell, an embryonic stem cell, a parenchymal cell, an epithelial cell, an endothelial cell, a mesothelial cell, a fibroblast, an osteoblast, a chondrocyte, an exogenous cell, an endogenous cell, a stem cell, a hematopoietic stem cell, a pluripotent stem cell, a bone marrow-derived progenitor cell, a progenitor cell, a myocardial cell, a skeletal cell, a fetal cell, an embryonic cell, an undifferentiated cell, a multi-potent progenitor cell, a unipotent progenitor cell, a monocyte, a cardiomyocyte, a cardiac myoblast, a skeletal myoblast, a macrophage, a capillary endothelial cell, a xenogenic cell, an allogenic cell, an adult stem cell, and a post-natal stem cell. In some aspects, the stem cells have the potential to differentiate into cardiac tissue cells. Thus, in some aspects, the stem cells can be pluripotent. In other aspects, the stem cells can be angioblasts or hemangioblasts. In additional aspects, the stem cells can be myoblasts. The stem cells described herein can be derived and maintained using standard methods for stem cell culture.

In another aspect, the additional component can be a drug, including any known or newly discovered substance that can be administered to the heart of a subject. For example, the additional component can be an antithrombotic agent, including, for example, and without limitation, antiplatelet drugs, anticoagulants, and thrombolytic drugs. Exemplary antiplatelet drugs include, for example and without limitation, Aspirin, Clopidogrel, Prasugrel, Ticlopidine, Cilostazol, Abciximab, Eptifibatide, Tirofiban, and Dipyridamole. Exemplary anticoagulants include, for example and without limitation, Coumadins, Acenocoumarol, Phenprocoumon, Phenindione, Heparin, Low Molecular Weight Heparin, Fondaparinux, Idraparinux, Agratroban, Lepirudin, Bivalirudin, and Dabigatran. Exemplary thrombolytic drugs include, for example and without limitation, Alteplase, Reteplase, Tenecteplase, Anistreplase, Streptokinase, and Urokinase.

In a further aspect, the additional component can be a protein. In this aspect, the additional component can be an exogenous protein, such as those normally found in mammalian ECM. Thus, it is contemplated that the additional component can be, for example and without limitation, a collagen, a proteoglycan, a glycosaminoglycan (GAG) chain, a glycoprotein, a growth factor, a cytokine, a cell-surface associated protein, a cell adhesion molecule (CAM), an angiogenic growth factor, an endothelial ligand, a matrikine, a matrix metalloprotease, a cadherin, an immunoglobulin, a fibril collagen, a non-fibrillar collagen, a basement membrane collagen, a multiplexin, a small-leucine rich proteoglycan, decorin, biglycan, a fibromodulin, keratocan, lumican, epiphycan, a heparan sulfate proteoglycan, perlecan, agrin, testican, syndecan, glypican, serglycin, selectin, a lectican, aggrecan, versican, nuerocan, brevican, cytoplasmic domain-44 (CD-44), macrophage stimulating factor, amyloid precursor protein, heparin, chondroitin sulfate B (dermatan sulfate), chondroitin sulfate A, heparan sulfate, hyaluronic acid, fibronectin (Fn), tenascin, elastin, fibrillin, laminin, nidogen/entactin, fibulin I, fibulin II, integrin, a transmembrane molecule, platelet derived growth factor (PDGF), epidermal growth factor (EGF), transforming growth factor alpha (TGF-alpha), transforming growth factor beta (TGF-β), fibroblast growth factor-2 (FGF-2) (also called basic fibroblast growth factor (bFGF)), thrombospondin, osteopontin, angiotensin converting enzyme (ACE), or a vascular epithelial growth factor (VEGF). Thus, in addition to one or more extracellular matrix tissues, the disclosed extracellular matrix material can comprise collagen I and III, elastin, laminin, CD44, hyaluronan, syndecan, bFGF, HGF, PDGF, VEGF, Fn, tenascin, heparin, heparan sulfate, chondroitin sulfate B, integrins, decorin, TGF-β, or a combination thereof.

It is contemplated that once the extracellular matrix material is in the body of the subject, at least a portion of the extracellular matrix material can integrate into the host tissue and develop substantially the same properties as proximate native material. Specifically, the extracellular matrix material can be in cellular communication with the blood supply of a subject. It is contemplated that at least 70% of the extracellular matrix material can fully integrate into the host tissue. More preferably, it is contemplated that at least 80% of the extracellular matrix material can fully integrate into the host tissue. Most preferably, it is contemplated that at least 90% of the extracellular matrix material can fully integrate into the host tissue.

It is contemplated that extracellular matrix material can be harvested and processed as described in U.S. Pat. No. 5,554, 389 (UBS), U.S. Pat. No. 6,099,567 (SS), and U.S. Pat. No.

6,379,710 (LBM), as well as U.S. Pat. No. 4,902,508, U.S. Pat. No. 4,956,178, U.S. Pat. No. 5,275,826, U.S. Pat. No. 5,516,533, U.S. Pat. No. 5,573,784, U.S. Pat. No. 5,711,969, U.S. Pat. No. 5,755,791, U.S. Pat. No. 5,955,110, U.S. Pat. No. 5,968,096, U.S. Pat. No. 5,997,575, and U.S. Pat. No. 6,653,291 (SIS), which are specifically incorporated by reference in their entirety. In one aspect, it is contemplated that the valve 12 and sewing ring 40 described herein can be stamped out of a sheet of extracellular matrix material. For example, and without limitation, it is contemplated that the valve 12 as depicted in FIGS. 1A and 1B, and the sewing ring as depicted in FIG. 3C, can be stamped out of a substantially planar sheet of extracellular matrix material. In an additional aspect, the valve 12 and the sewing ring 40 can be continuous and can be formed or stamped out of a plane of laminate sheets of matrix material. In another aspect, the extracellular matrix material can be single sheets, multi-laminate sheets, or some other configuration of extracellular matrix that lends itself to the formation of sheet-like leaflets. For example and without limitation, the valve 12 and the sewing ring 40 can be stamped out of a larger laminate sheet of 2 ply, 3 ply, 4, ply, 5 ply, 6 ply, 7 ply, 8 ply, 9 ply, and 10 ply extracellular matrix. It is further contemplated that the extracellular matrix material can be selectively formed at an appropriate width for the valve being replaced.

In a further aspect, the extracellular matrix material of the valve 12 and sewing ring 40 can have a desired elastic modulus. For example, and without limitation, the desired elastic modulus of the extracellular matrix material can range from about 5 to about 15, more preferably from about 7 to about 13; and most preferably from about 8 to about 12. It is contemplated that the desired elastic modulus can be selected to substantially correspond to the elastic modulus of native tissue surrounding the site of implantation of the valve, thereby improving integration of the valve into the host tissue. It is contemplated that the source of the extracellular matrix material, including, for example and without limitation, urinary bladder submucosa, small intestine submucosa, stomach submucosa, and liver basement membrane, can be selected depending on the desired elastic modulus.

Figure 8A:
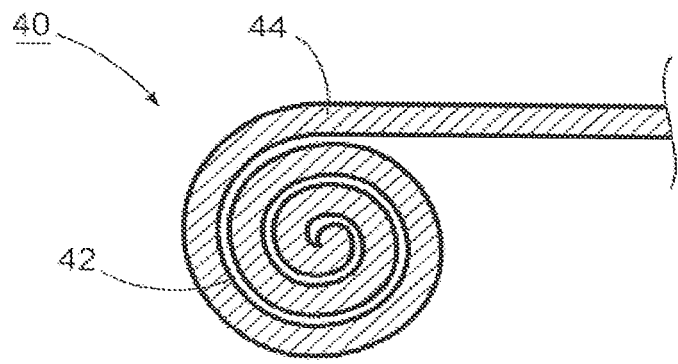
FIG. 8A depicts a cross-sectional view of an exemplary sewing ring rolled from a piece of extracellular material, as described herein.
Figure 8B:
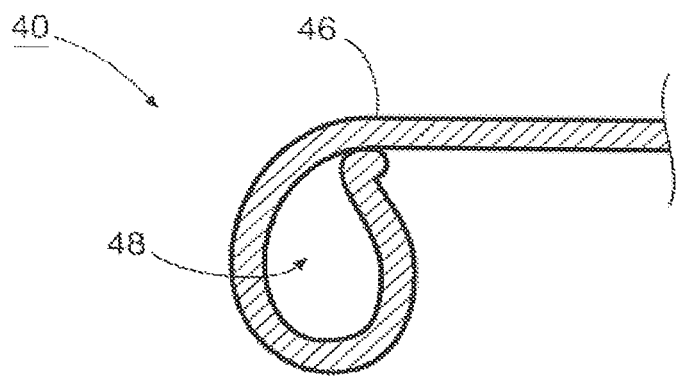
FIG. 8B depicts a cross-sectional view of an exemplary sewing ring formed into a tear drop shape, as described herein.
Figure 8C:
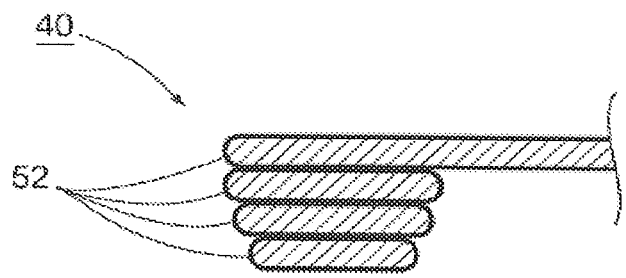
FIG. 8C depicts a cross-sectional view of an exemplary sewing ring having a plurality of laminated sheets of extracellular matrix material.

In one aspect, FIG. 8A depicts a sewing ring 40 constructed from a rolled piece of extracellular matrix material as described herein. In this aspect, the rolled piece of extracellular matrix material can define a cross-sectional core 42. The sewing ring 40 can have a point of attachment 44 where two ends of the sewing ring are attached to one another. In another aspect, and referring to FIG. 8B, the sewing ring 40 can be defined by a tightly configured roll of extracellular matrix material. In this aspect, the extracellular matrix material can be folded to itself and attached at point 46 with suture or glue or other attachment means. The sewing ring 40 can have a cross-sectional core 48 that illustrates the resulting tear-drop configuration of the sewing ring when it is attached to itself. In another aspect, as shown in FIG. 8C, the sewing ring 40 can be formed from a plurality of laminated sheets 52 of extracellular matrix material. It is contemplated that the plurality of sheets 52 of extracellular matrix material can comprise multiple types of extracellular matrix material, as described herein. It is further contemplated that the sheets 52 of extracellular material can be laminated together using any conventional biocompatible means for lamination of two structures. For example, it is contemplated that the sheets 52 of extracellular material can be laminated together using a biodegradable material.

In exemplary aspects, it is contemplated that the sewing ring 40 can be attached to the attachment surface defined by the outer edge portion 15 of the valve 12 as described herein. It is further contemplated that the outer edge portion 15 of the valve 12 can be formed in the same manner as the sewing ring 40, as described herein, to thereby define the attachment surface, which can be configured for attachment to a sewing ring or for direct attachment to the inner surface of the annulus 2.

In an additional aspect, it is contemplated that the sewing ring can have a minimal width compared to the area defined by the annulus. In this aspect, the width of the sewing ring can be less than about 5 mm, and more preferably less than about 1 mm. It is still further contemplated that the tight fit between the sewing ring and the annulus, coupled with the minimal width of the sewing ring, can maximize the portion of the lumen available for accommodating blood flow following attachment of the valve in the biased position.

It is contemplated that the extracellular matrix material of the sewing ring can be used with the leaflets of a trileaflet valve or with other valves such as pulmonary, aortic, mitral or tricuspid valves. The sewing ring can be used with mechanical or tissue valves.

In addition to comprising extracellular matrix material, the sewing ring 40 can further comprise metal, or a mixture of conventional metals or alloys. In one aspect, the sewing ring can also comprise a shape memory activated (SMA) material such as, for example and without limitation, Nitinol or other conventional SMA materials. It is contemplated that the sewing ring can be a synthetic or polymeric material, such as, for example and without limitation, silicone, rubber, plastic, or the like. In one aspect, the sewing ring can be constructed like catheter tubing, with a woven support of metal wire embedded within the reinforced plastic of the tubing. In another exemplary aspect, the sewing ring can comprise an extracellular matrix material and a conventional polymeric material. In this aspect, it is contemplated that the extracellular matrix material can be subjected to a conventional electrospinning process and then applied to the polymeric material to produce the sewing ring.

In one aspect, it is contemplated that the sewing ring can comprise a biodegradable material. In this aspect, it is contemplated that the biodegradable material can be configured to degrade following significant integration of the extracellular matrix material into the host tissue of the subject. More generally, it is contemplated that the sewing ring can be made of any material suitable for the purpose identified in the definition of a sewing ring. It is further contemplated that the functionality of the sewing ring can be maintained by ensuring that the sewing ring possesses sufficient flexibility to permit the larger circumference of the sewing ring to be placed into the smaller circumference of the annulus in a non-planar attachment configuration.

It is further contemplated that each configuration of the sewing ring imparts different advantages, and it is contemplated that different valves will be more or less appropriately suited for the different variations of sewing ring. For example, the sewing ring 40 of rolled extracellular matrix has a point where the ring is attached to itself. It is contemplated that this point of attachment would be considered a weak point in the sewing ring, and the ring needs to be attached to itself and the annulus with particular care and reinforcement so that the ring does not yield or break free at the point of attachment. Accordingly, it is contemplated that because sewing ring 40, while unitary, is non-tubular, attachment of the ring to the annulus will require attendant care to that aspect of its configuration. In one aspect, it is specifically contemplated that running sutures that surround the ring 40 will securely attach the ring to the annulus. Optionally, suturing through the ring itself can be used. This securing methodology may be difficult due to the dense and strong nature of the extracellular matrix material. However, it is contemplated that sutures can be accomplished with conventional stitches or mattress stitches depending on the surgeon's assessment of the situation.

It is still further contemplated that attachment of the valve can be accomplished percutaneously without open heart surgery. In use, the valve can be guided to the site of replacement after the defective valve has been removed, and the sewing ring can be systematically sutured or otherwise attached to the annular region in a biased position as described herein, using a visualization technique enabling manipulations in the body within the view of a camera that shows the manipulations to the surgeon.

In further aspects, methods are provided for using the valves and replacement leaflets as described herein to control fluid flow in a lumen having an annulus. In one aspect, the methods comprise providing at least one replacement leaflet having the characteristics of the leaflets described herein. In another aspect, the methods comprise securely attaching the at least one replacement leaflet to the annulus in a desired position. It is contemplated that the at least one leaflet can comprise a single leaflet that is used to replace a single defective leaflet located therein an annulus in a heart of a subject with a blood supply. It is further contemplated that the at least one replacement leaflet can promote vascular development within the subject by permitting cellular communication between the at least one leaflet and the blood supply of the subject. Thus, it is further contemplated that the at least one replacement leaflet can effectively behave as a native leaflet after attachment in the desired position within the subject's heart.

In another aspect, the method can comprise providing a valve as described herein. In this aspect, the method can comprise securely attaching the outer portion of the valve to the annulus in a biased position as described herein. Optionally, in an additional aspect, the valve can comprise a sewing ring as described herein. In this aspect, the method can comprise securely attaching the outer portion of the sewing ring to the annulus such that the valve is in a biased position as described herein.

In a further aspect, a kit having a valve as described herein can be assembled. Optionally, the kit can comprise a sewing ring as described herein. Additionally, it is contemplated that the sewing rings as described herein can be provided separately for attaching any number of valves.

Experimental Data in Support of Concept

In one long-term animal study, four clinically normal swine were used to study the effectiveness of porcine small intestine submucosa as cardiac pulmonary valve leaflets. Matheny, et al., *Porcine Small Intestine Submucosa as a Pulmonary Valve Leaflet Substitute*, The Journal of Heart Valve Disease 2000; 9:769-775. In this study, each swine had one pulmonary valve leaflet excised and replaced with a leaflet produced from a layer of porcine small intestine submucosa. The leaflets were secured within the annulus using a suture line. The swine were individually sacrificed at 56, 63, 88, and 111 days following implantation of the leaflets.

The leaflet removed 63 days after implantation was securely attached to the annulus along the entire suture line. Although one fenestration was present, complete organization of the leaflet was observed. The apical portion of the leaflet consisted of mature and moderately dense fibrous connective tissue, while the basal portion of the leaflet had less dense and mucinous tissue. Complete endothelialization of the leaflet was observed.

The leaflet removed 88 days after implantation was also securely attached to the annulus along the entire suture line. No fenestrations were present, and the basal portion of the leaflet was cellular and mature connective tissue. The apical portion of the leaflet was notably larger in comparison to the leaflet removed 63 days after implantation. The apical portion formed a largely acellular nodule composed of serum, cellular debris, and leukocytes in a dense network of fibrin (an organized thrombus). A layer of residual and acellular matrix was observed at the center of the thrombus. Endothelial cell coverage of the leaflet was continuous.

The leaflet removed 111 days after implantation was securely and continuously attached to the annulus along the entire suture line without evidence of thrombus. The leaflet was observed to possess gross characteristics similar to those of normal leaflet tissue. Specifically; the leaflet was observed to have histologically identifiable features and was composed of collagenous tissue containing indistinct layers of viable cells. The histological organization of the leaflet was comparable to the organization observed in the adjacent native leaflets. The surfaces of the leaflet were completely lined with endothelial cells.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is therefore understood that the invention is not limited to the specific embodiments disclosed herein, and that many modifications and other embodiments of the invention are intended to be included within the scope of the invention. Moreover, although specific terms are employed herein, they are used only in a generic and descriptive sense, and not for the purposes of limiting the described invention.

Various publications are referenced in this document. These publications in their entireties are hereby incorporated by reference into this application in order to more fully describe the state of the art to which the disclosed system and method pertains. The references disclosed are also individually and specifically incorporated by reference herein for the material contained in them that is discussed in the sentence in which the reference is relied upon.

What is claimed is:

1. A valve for controlling fluid flow in a lumen having an annulus, the valve and the annulus each having a circumference, the annulus having an interior wall, the valve comprising:
   a body defining an outer edge portion, wherein the valve is substantially planar in an unstressed position, wherein an operative diameter of the valve in the unstressed position is larger than the diameter of the annulus;
   a plurality of leaflets disposed on the outer edge portion of the valve, wherein, in the unstressed position, the plurality of leaflets are substantially planar; and
   the outer edge portion of the valve being attached to the interior wall of the annulus in a biased position, wherein, in the biased position, the outer edge portion of the valve is substantially non-planar, the plurality of leaflets are substantially non-planar, and at least a portion of at least one leaflet of the plurality of leaflets is superposed relative to at least a portion of at least one of the adjacent leaflets of the plurality of leaflets, and wherein, in the biased position, a distal end portion of each leaflet of the plurality of leaflets extends radially inwardly generally toward a center point in the valve, wherein at least a portion of each leaflet of the plurality of leaflets comprises extracellular matrix material.

\* \* \* \* \*